United States Patent

Leise, Jr. et al.

(10) Patent No.: US 6,726,667 B2
(45) Date of Patent: Apr. 27, 2004

(54) DRAINABLE OSTOMY POUCH AND CLOSURE MEANS THEREFOR

(75) Inventors: Walter F. Leise, Jr., Lindenhurst, IL (US); Michael A. Metz, Chicago, IL (US)

(73) Assignee: Hollister Incorporated, Libertyville, IL (US)

( * ) Notice: Subject to any disclaimer, the term of this patent is extended or adjusted under 35 U.S.C. 154(b) by 125 days.

(21) Appl. No.: 10/171,165

(22) Filed: Jun. 13, 2002

(65) Prior Publication Data

US 2003/0028160 A1 Feb. 6, 2003

Related U.S. Application Data

(60) Provisional application No. 60/298,492, filed on Jun. 15, 2001.

(51) Int. Cl.[7] ................................................. A61F 5/44
(52) U.S. Cl. ........................................ 604/339; 604/335
(58) Field of Search .............................. 604/277, 327, 604/332–345, 355; 383/33; 150/900

(56) References Cited

U.S. PATENT DOCUMENTS

| | | | |
|---|---|---|---|
| 3,523,534 A | | 8/1970 | Nolan |
| 3,825,005 A | | 7/1974 | Fenton |
| 3,897,780 A | * | 8/1975 | Trousil ........................ 604/344 |
| 4,439,191 A | * | 3/1984 | Hogan ......................... 604/332 |
| 4,441,659 A | | 4/1984 | Marklund |
| 4,460,359 A | * | 7/1984 | Fenton ......................... 604/277 |
| 4,596,566 A | * | 6/1986 | Kay ............................. 604/343 |
| 4,755,177 A | * | 7/1988 | Hill .............................. 604/336 |
| 4,983,172 A | * | 1/1991 | Steer et al. ................... 604/332 |
| 4,988,343 A | * | 1/1991 | Ballan ......................... 604/332 |
| 5,044,774 A | | 9/1991 | Bullard et al. |
| 5,968,024 A | * | 10/1999 | Freeman ...................... 604/334 |
| 6,336,918 B1 | * | 1/2002 | Olsen et al. ................. 604/332 |
| 6,544,241 B2 | * | 4/2003 | Morton ........................ 604/334 |
| 2002/0010444 A1 | * | 1/2002 | Wiltshire et al. ............ 604/335 |
| 2002/0165507 A1 | * | 11/2002 | Hessel et al. ................ 604/342 |
| 2003/0073962 A1 | * | 4/2003 | Olsen et al. ................. 604/327 |
| 2003/0167042 A1 | * | 9/2003 | Poulsen ....................... 604/327 |

FOREIGN PATENT DOCUMENTS

| | | |
|---|---|---|
| GB | 2 346 328 A | 8/2000 |
| WO | WO 01/28470 | 4/2001 |

\* cited by examiner

*Primary Examiner*—Weilun Lo
*Assistant Examiner*—Michael Bogart
(74) *Attorney, Agent, or Firm*—Marshall, Gerstein & Borun LLP

(57) ABSTRACT

A drainable ostomy pouch having at least one arcuate spring member, and preferably two such spring members, adjacent the discharge opening at the lower end of the pouch is disclosed. Each wall of the pouch with such arcuate spring member is normally bowed outwardly from the other wall to hold the discharge opening in open condition for draining of the pouch's contents. To seal the discharge opening, the lower end of the pouch is folded upwardly to force the spring member(s) into flattened condition, and the pouch's lower end is then secured in such upwardly-folded condition.

11 Claims, 1 Drawing Sheet

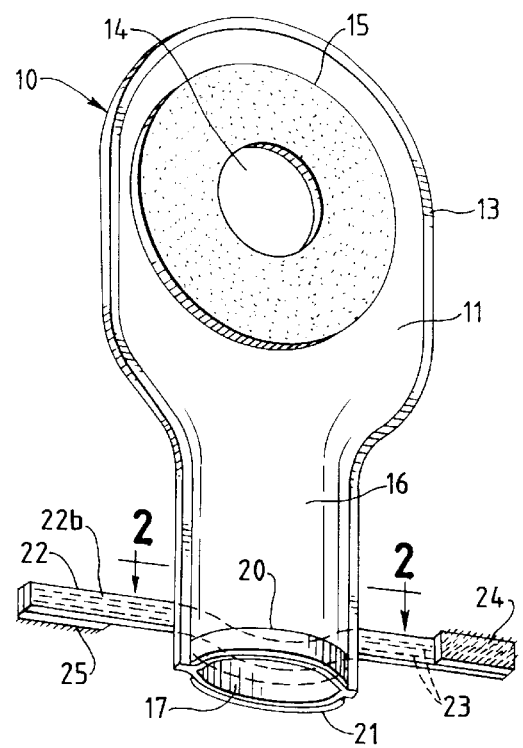
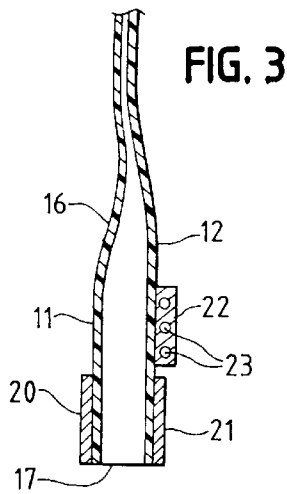
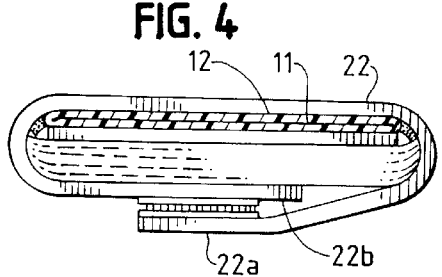
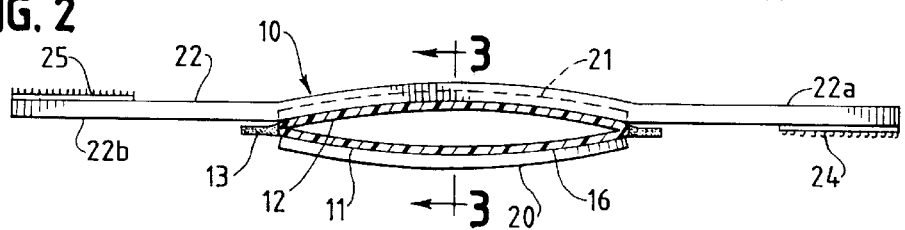
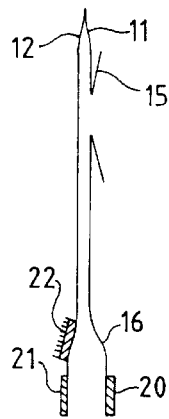
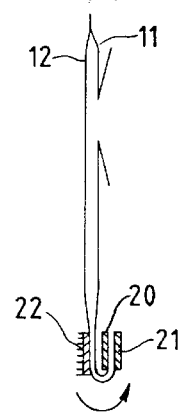
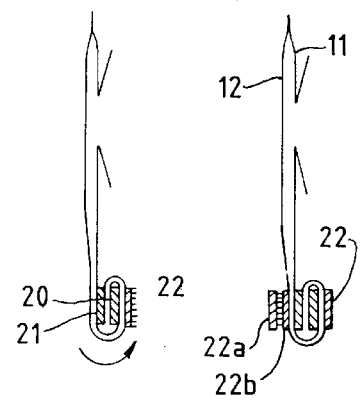

DRAINABLE OSTOMY POUCH AND CLOSURE MEANS THEREFOR

RELATED APPLICATION

We claim priority to, and are entitled to the benefit of, the filing date of Provisional Application No. 60/298,492, filed Jun. 15, 2001, as to all subject matter commonly disclosed therein.

BACKGROUND

Drainable ostomy pouches are well known as shown, for example, in Nolan U.S. Pat. No. 3,523,534 and Jensen et al. U.S. Pat. No. 4,441,659. Such a pouch typically has flat opposing side walls secured together along their edges and defining a chamber for receiving body waste material. One of the walls is provided with a stoma-receiving opening, and means are provided for securing the pouch to a patient's abdomen so that waste discharged from the stoma is received in the chamber. At its lower end, the drainable pouch has a discharge opening, usually provided at the lower end of a narrowed neck portion, and means are provided for maintaining the discharge opening in sealed condition until waste material is to be drained from the pouch. Such closure means may take the form of a clamp, as in the aforementioned Nolan patent, or some device for securing the neck portion in upwardly-rolled condition. Conventional wire ties or wraps have been used for that purpose.

A drainable pouch is reuseable and must be periodically emptied of its contents. Cleaning is necessary prior to reuse so that effective sealing can be assured and odors emanating from the resealed pouch can be avoided. Users often encounter difficulty and discomfort in unsealing, emptying, cleaning and resealing drainable pouches because of the direct exposure to waste matter and because the manipulations may require greater dexterity than a patient, particularly an elderly patient, can provide. Adding to the problem is the fact that residual amounts of solid and/or liquid waste matter at the lower end of a drainable pouch tend to block or hold the walls of the pouch together, making cleaning of the inside surfaces adjacent the drain opening even more difficult.

SUMMARY OF THE INVENTION

The drainable pouch of this invention has conventional side walls of flexible plastic film joined together along their edges and providing a downwardly extending neck portion terminating in a discharge opening. The walls of the pouch adjacent the discharge opening are provided with arcuate transversely-extending spring members which are normally bowed away from each other to hold the discharge opening in open condition. The spring members preferably take the form of curved plastic strips secured along their length to each wall of the pouch adjacent the discharge opening. To close the pouch, a user simply squeezes the strips together into straightened parallel condition and then rolls or folds the neck portion upwardly two or more times.

Means are provided for releasably maintaining the neck portion in its rolled or folded condition. In a preferred embodiment of this invention, such means takes the form of a foldable wire tie strap secured to one of the walls of the neck portion at a point spaced above the spring members. The strap has end portions that extend laterally a substantial distance beyond each of the side edges of the neck portion. After the neck portion has been rolled upwardly, the end portions of the tie strap are folded into overlapping condition over the roll, and means provided by the overlapping end portions of the tie strap releasably lock those end portions together to prevent unrolling of the pouches neck portion.

In a preferred embodiment, the means for releasably securing together the overlapping end portions of the tie strap takes the form of hook-loop (i.e. Velcro-type) patches, but other means for holding the end portions together in overlapping condition might be provided.

Other features and advantages of the invention will become more apparent from the drawings and description.

DRAWINGS

FIG. 1 is a perspective view of a drainable pouch equipped with the spring elements and closure means of the present invention.

FIG. 2 is an enlarged cross sectional view taken along line 2—2 of FIG. 1.

FIG. 3 is a cross sectional view taken along line 3—3 of FIG. 2.

FIG. 4 is a sectional view of the structure of FIG. 2 but showing the tie strap in folded condition for holding the spring elements in straightened condition and the discharge opening of the pouch in closed condition.

FIGS. 5–9 are schematic views illustrating the steps of closing, and securing in closed condition, the drainage neck of the ostomy pouch of this invention.

It is to be understood that for clarity of illustration, all Figures appearing in this application are at least somewhat schematic. Thus, in FIGS. 1–4, for clarity of illustration, the parts are shown as having greater thickness than would be expected in actual practice, with the result that the cross sectional view of FIG. 4 depicts the folded neck of the pouch as having a thickness that is considerably exaggerated. FIGS. 5–9 are simplified schematic drawings with the walls of the pouch represented by single lines so as to show more clearly the manipulative steps involved in securing the pouch in closed condition.

DETAILED DESCRIPTION OF PREFERRED EMBODIMENTS

Referring to the drawings, the numeral 10 generally designates a drainable ostomy pouch having side walls 11 and 12 formed of a flexible plastic film that is water and gas (odor) impervious. The walls are sealed together along their edges as indicated at 13, and one of the walls 11 is provided with a stoma-receiving opening 14 surrounded by means for attaching the pouch to a patient. Such means may take the form of an adhesive-coated attachment ring 15, making the pouch a one-piece appliance, or alternatively, the means may take the form of a coupling ring for detachably securing the pouch to an adhesive faceplate equipped with a mating coupling ring. In the latter case, the pouch would constitute one component of a two-piece appliance, all as well understood in the art.

The pouch has an elongated downwardly-extending neck portion 16 terminating at its lower end in a discharge opening 17. In the embodiment shown in the drawings, each wall of the neck portion 16 is provided with an arcuate, transversely-extending, spring member 20, 21. Each spring member is located immediately adjacent the discharge opening 17 and substantially spans the distance between the sealed edge portions 13 of the neck portion. While the members may be formed of any spring-like material, including metal, it is preferred that they be formed of any of a variety of relatively stiff, tough, and flexible plastic materials such as, for example, nylon. Each spring member is secured to or embedded in a wall of the pouch so that it bows away from the other member and forces the discharge opening of the pouch into a normally open condition. However, by exerting finger pressure in the direction of the arrows in FIG. 6, the spring members may be squeezed towards each other into straightened condition, thereby closing the opening at the pouch's lower end.

It should be emphasized that when the spring members 20 and 21 are in their relaxed state, as shown most clearly in FIG. 2, their curvatures are smooth, uniform, and gradual, causing the walls of the neck portion to bow outwardly a limited distance from each other. Since the curvature of each member is smooth and gradual, straightening of those members can be readily accomplished by limited finger pressure to cause opposing inner surfaces of the neck adjacent the discharge opening into substantially uniform sealing contact with each other. To achieve such action, it is important that both of the gradually-curved spring members be secured along their full length by adhesive or other appropriate sealing means to corresponding surfaces (preferably the outer surfaces) of the walls of the neck or be embedded for their full length in the material of such walls. Also, the gradual curvatures of the two spring members in their relaxed state are preferably the same but in opposite directions.

The means for holding the spring members in straightened parallel condition comprises rolling the lower end of the neck upwardly two or more times as depicted in FIGS. 7 and 8. The rolling action effectively seals the drainage opening 17. Securing means are then provided for releasably securing the pouch's neck portion in its upwardly rolled or folded condition.

In the embodiment shown in the drawings, the means for maintaining the neck in rolled condition takes the form of tie strap 22. The tie strap may be formed of flexible plastic material and preferably has metal strands or wires 23 extending longitudinally through it. In the illustration given, the strap 22 has its mid portion secured to wall 12 of the pouch but, alternatively, the strap might be secured to wall 11, that is, the same wall in which stoma-receiving opening 14 is provided. If desired, one or both sides of the strap may be covered with a resilient plastic foam or other soft protective covering material(not shown) to prevent skin irritation, especially over extended periods of contact.

Of particular importance is the fact that the strap has end portions 22a and 22b that extend laterally outwardly beyond the side edges of the neck portion a sufficient distance so that the end portions may be folded over each other into overlapping condition as illustrated in FIG. 4. The opposing surfaces of the overlapping end portions are provided with interconnecting means, preferably in the form of hook/loop (i.e. Velcro-type) zones or patches 24 and 25. Therefore, when the lower end of the neck portion has been rolled upwardly as shown in FIGS. 8 and 9, end portions 22a and 22b may be interlocked together to maintain the neck portion in folded and sealed condition.

While Velcro-type attachment patches are believed to be particularly effective in securing the end portions of the strap together, other attachment means for holding the end portions in overlapping condition might instead be used. For example, pressure-sensitive adhesive coatings for releasably securing the end portions together may be used. Or, one end portion might be provided with a longitudinal series of openings and the other with lugs or insert elements receivable in such openings (not shown). Alternatively, spring snaps might be provided by the respective end portions to receive somewhat similar results (not shown).

It should be observed that the strap 22 is secured to wall 12 of the pouch at a predetermined distance above the pouch's lower end and above spring members 20 and 21. In the embodiment illustrated, the distance is slightly greater than the width of the strap (also from the pouch's lower end the width of each of the spring elements 20 and 21). Ideally, the spacing between strap 22 and spring member 21 is just sufficient to position the strap 22 at the same elevation as the spring members 20 and 21 after a single upward fold of the neck portion as depicted in FIG. 7. After the second fold (FIG. 8), strap 22 is positioned along the bodyside wall 11 of the pouch, allowing its end portions to be folded over and joined together over the opposite wall 12 of the pouch. It is to be understood, however, that the strap might be positioned upwardly at even greater distance from the neck's lower end so as to allow the neck portion to be rolled or folded upwardly more than twice before the strap is in position to be wrapped about the roll.

In the preferred embodiment of the invention illustrated in drawings, two spring elements 20 and 21 are provided. Such an arrangement ensures that the neck portion of the pouch will expand into the opened condition shown in FIGS. 1–3 when the neck has been unrolled for discharging the contents of the pouch. However, it is believed that somewhat similar results, although possibly less effective, might be achieved by providing only a single spring element on one of the walls. Such a construction would be achieved, for example, by eliminating spring element 21 from the preferred embodiment, leaving only a single arcuate spring element 20.

By biasing the lower end of the pouch into a normally open condition, the spring elements make it easier for a user to drain the contents from the pouch and to clean the surfaces of the neck portion before restoring the pouch to its folded and sealed condition.

While in the foregoing we have disclosed embodiments of the invention in considerably detail for purposes of illustration, it will be understood by those skilled in the art that many of those details might be varied without departing from the spirit and scope of the invention.

What is claimed is:

1. A drainable ostomy pouch having generally parallel sidewalls of flexible sheet material joined along their edges to define a chamber therebetween and having a downwardly extending neck portion terminating in a discharge opening for draining the contents from said chamber said pouch being closed by securing the walls of said neck portion together at said opening and by folding said neck portion upwardly; wherein the improvement comprises at least one of said walls of said neck portion being provided with an arcuate, transversely-extending spring member immediately adjacent said discharge opening; said spring member and said one wall normally being bowed outwardly away from the other of said walls of said neck portion to hold said discharge opening in a normally open condition but being flexible under finger pressure into a straightened condition for closing said opening; and means for selectively holding said spring member in straightened condition.

2. The drainable ostomy pouch of claim 1 in which said means for holding said spring member in straightened condition comprises rolling said neck portion upwardly at least twice; and means for releasably securing said neck portion in its upwardly rolled condition.

3. The drainable ostomy pouch of claim 2 in which said means for securing said neck portion in upwardly rolled condition comprises a foldable tie strap secured to one of said walls of said neck portion along a transverse line spaced above said spring member; said strap having end portions extending laterally outwardly beyond the side edges of said neck portion; said end portions of said strap being foldable into overlapping condition with respect to each other; and means for releasably holding said end portions of said strap in overlapping condition.

4. The drainable ostomy pouch of claim 3 in which said means for releasably securing said end portions in overlapping condition comprises interengaging hook-loop contact patches on opposing surfaces of said end portions.

5. The drainable ostomy pouch of claims 1, 2 or 3 in which said spring member comprises a smoothly and gradually curved arcuate strip of stiff but flexible plastic material.

6. A drainable ostomy pouch having generally parallel side walls of flexible sheet material joined along their edges to define a cavity therebetween and having a downwardly-extending neck portion terminating in a discharge opening for draining the contents from said cavity; said pouch being closed by securing the walls of said neck portion together at said opening and by, folding said neck portion upwardly; wherein the improvement comprises each of said walls of said neck portion being provided with an arcuate, transversely extending spring member immediately adjacent said discharge opening; each of said spring members being secured along their entire length to opposite walls of the pouch and being curved smoothly and gradually away from each other to hold said discharge opening in open condition when said spring members are in a relaxed state; said spring members being flexible under finger pressure into straightened condition for closing said opening; and means for selectively holding said spring members in straightened condition.

7. The drainable ostomy pouch of claim 1 in which said means for holding said spring members in straightened condition comprises rolling said neck portion upwardly at least twice; and means for releasably securing said neck portion in its upwardly rolled condition.

8. The drainable ostomy pouch of claims 6 or 7 in which said spring members are of the same size and curvature when the same are in a relaxed state to cause the walls of the said neck portion at said discharge opening to bow outwardly away from each other.

9. The drainable ostomy pouch of claims 6 or 7 in which said spring members each comprises a smoothly and gradually curved arcuate strip of stiff but flexible plastic material.

10. The drainable ostomy pouch of claims 6 or 7 in which said means for securing said neck portion in upwardly rolled condition comprises a foldable tie strap secured to one of said walls of said neck portion along a transverse line spaced above said spring members; said strap having end portions extending laterally outwardly beyond the side edges of said neck portion; said end portions of said strap being foldable into overlapping condition with respect to each other; and means for releasably holding said end portions of said strap in overlapping condition.

11. The drainable ostomy pouch of claim 10 in which said means for releasably securing said end portions in overlapping condition comprises interengaging hook-loop contact patches on opposing surfaces of said end portions.

* * * * *